(12) United States Patent
Jaworek

(10) Patent No.: US 8,758,235 B2
(45) Date of Patent: Jun. 24, 2014

(54) FOLDABLE SURGICAL RETRACTOR

(75) Inventor: Jacqueline A. Jaworek, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/546,123

(22) Filed: Jul. 11, 2012

(65) Prior Publication Data

US 2013/0018229 A1    Jan. 17, 2013

Related U.S. Application Data

(60) Provisional application No. 61/507,262, filed on Jul. 13, 2011.

(51) Int. Cl.
*A61B 1/32* (2006.01)

(52) U.S. Cl.
USPC ............................. 600/206; 600/208; 600/225

(58) Field of Classification Search
USPC .................................................. 600/184–246
See application file for complete search history.

(56) References Cited

U.S. PATENT DOCUMENTS

| | | | |
|---|---|---|---|
| 3,774,596 A | 11/1973 | Cook | 128/5 |
| 3,807,393 A | 4/1974 | McDonald | 128/20 |
| 3,863,639 A | 2/1975 | Kleaveland | 128/303 |
| 4,190,042 A | 2/1980 | Sinnreich | 128/20 |
| 4,889,107 A | 12/1989 | Kaufman | 128/20 |
| 5,425,357 A | 6/1995 | Moll et al. | 128/20 |
| 5,501,653 A | 3/1996 | Chin | 600/204 |
| 5,743,851 A | 4/1998 | Moll et al. | 600/204 |
| 6,036,640 A | 3/2000 | Corace et al. | 600/207 |
| 6,605,037 B1 | 8/2003 | Moll et al. | 600/204 |
| 7,052,454 B2 * | 5/2006 | Taylor | 600/114 |
| 7,704,207 B2 | 4/2010 | Albrecht et al. | 600/208 |
| 7,766,823 B2 | 8/2010 | Moll et al. | 600/192 |
| 8,128,559 B2 | 3/2012 | Minnelli | 600/206 |
| 2004/0054353 A1 | 3/2004 | Taylor | |
| 2005/0283050 A1 | 12/2005 | Gundlapalli et al. | 600/208 |

(Continued)

FOREIGN PATENT DOCUMENTS

| EP | 2 283 778 A2 | 7/2010 | A61B 17/02 |
|---|---|---|---|
| GB | 2 071 502 A | 3/1980 | A61B 17/02 |

(Continued)

OTHER PUBLICATIONS

International Search Report for PCT/US 92/04392, dated Sep. 12, 1992.

(Continued)

*Primary Examiner* — Mary Hoffman
*Assistant Examiner* — Christina Negrellirodrigue
(74) *Attorney, Agent, or Firm* — Brinks Gilson & Lione

(57) ABSTRACT

A foldable retractor is provided. The retractor includes an arcuate deformable frame that is defined from a first arm extending through a first portion of an outer circumference of the frame, and a second arm that defines a remaining portion of the outer circumference. The first and second arms each include opposite first and second end portions, wherein the respective first end portions and the respective second end portions are hingedly connected together. The first and second arms of the frame are biased toward a first configuration wherein the combined first and second arms are aligned substantially continuously through the combined first and second end portions and the frame extends through substantially a single plane.

16 Claims, 8 Drawing Sheets

(56) References Cited

U.S. PATENT DOCUMENTS

| | | | |
|---|---|---|---|
| 2007/0078477 A1 | 4/2007 | Heneveld, Sr. et al. | 606/191 |
| 2008/0021362 A1 | 1/2008 | Fihe et al. | 602/75 |
| 2009/0082633 A1 | 3/2009 | Kathrani et al. | 600/207 |
| 2009/0137877 A1 | 5/2009 | Minnelli et al. | 600/204 |
| 2009/0287046 A1 | 11/2009 | Yamatani | 600/104 |
| 2010/0087713 A1 | 4/2010 | Eliash | 600/206 |
| 2010/0113882 A1 | 5/2010 | Widenhouse et al. | 600/208 |
| 2010/0228090 A1 | 9/2010 | Weisenburgh, II et al. | 600/201 |
| 2010/0228093 A1 | 9/2010 | Voegele et al. | 600/204 |
| 2011/0034777 A1 | 2/2011 | Ames et al. | 600/206 |
| 2011/0105848 A1 | 5/2011 | Sadovsky et al. | 600/204 |
| 2011/0172495 A1 | 7/2011 | Armstrong | 600/233 |

FOREIGN PATENT DOCUMENTS

| | | | |
|---|---|---|---|
| WO | WO 92/21291 | 10/1992 | A61B 17/02 |
| WO | WO 2005/104959 A2 | 10/2005 | A61B 17/02 |
| WO | WO 2009/034922 A1 | 3/2009 | |
| WO | WO 2010/094799 A1 | 8/2010 | A61B 17/02 |

OTHER PUBLICATIONS

International Search Report for EP 12 18 7293, dated Jan. 21, 2013.
International Search Report and Written Opinion for PCT/US2012/046141, dated Nov. 27, 2012.
International Preliminary Report on Patentability and Written Opinion for PCT/US2012/046141, dated Jan. 14, 2014.

* cited by examiner

FOLDABLE SURGICAL RETRACTOR

CROSS-REFERENCE TO RELATED APPLICATIONS

This application claims priority under 35 U.S.C. 119(e) to U.S. Provisional Application No. 61/507,262, filed on Jul. 13, 2011, the entirety of which is hereby fully incorporated by reference herein.

TECHNICAL FIELD

Surgical retractors are normally provided to assist with opening a surgical field to provide a physician access to perform a medical procedure within the surgical field, as well as to move unwanted tissue away from the surgical field. The use of a surgical retractor prevents damage to the unwanted tissue as well as provides room within the surgical field for the physician to perform the desired procedure.

SUMMARY

A first representative aspect of the disclosure is provided. The first aspect includes a foldable retractor. The retractor includes an arcuate deformable frame that is defined from a first arm extending through a first portion of an outer circumference of the frame, and a second arm that defines a remaining portion of the outer circumference. The first and second arms each include opposite first and second end portions, wherein the respective first end portions and the respective second end portions are hingedly connected together. The first and second arms of the frame are biased toward a first configuration wherein the combined first and second arms are aligned substantially continuously through the combined first and second end portions and the frame extends through substantially a single plane.

Another representative aspect of the disclosure is provided. The aspect includes a foldable retractor. The retractor includes a relatively flexible frame that includes a first arm defining a first portion of a circumference of the frame, and a second arm defining a remaining portion of the circumference of the frame. Each of the first and second arms comprising first and second end portions are disposed upon opposite ends of the respective first and second arm. Each of the first end portions are hingedly connected together and each of the second end portions are hingedly connected together such that the frame is biased to a first relatively planar configuration. The first and second arms may be folded with respect to each other to a second configuration wherein the first and second arms are disposed in substantially the same orientation. A deformable membrane is secured around at least a portion of the arcuate frame to form a restraining structure across a central opening of the frame, wherein the membrane urges the first and second arms into the first orientation.

Advantages of the disclosed retractor will become more apparent to those skilled in the art from the following description of embodiments that have been shown and described by way of illustration. As will be realized, other and different embodiments are contemplated, and the disclosed details are capable of modification in various respects. Accordingly, the drawings and description are to be regarded as illustrative in nature and not as restrictive.

DETAILED DESCRIPTION OF PREFERRED EMBODIMENTS

Figure 1:
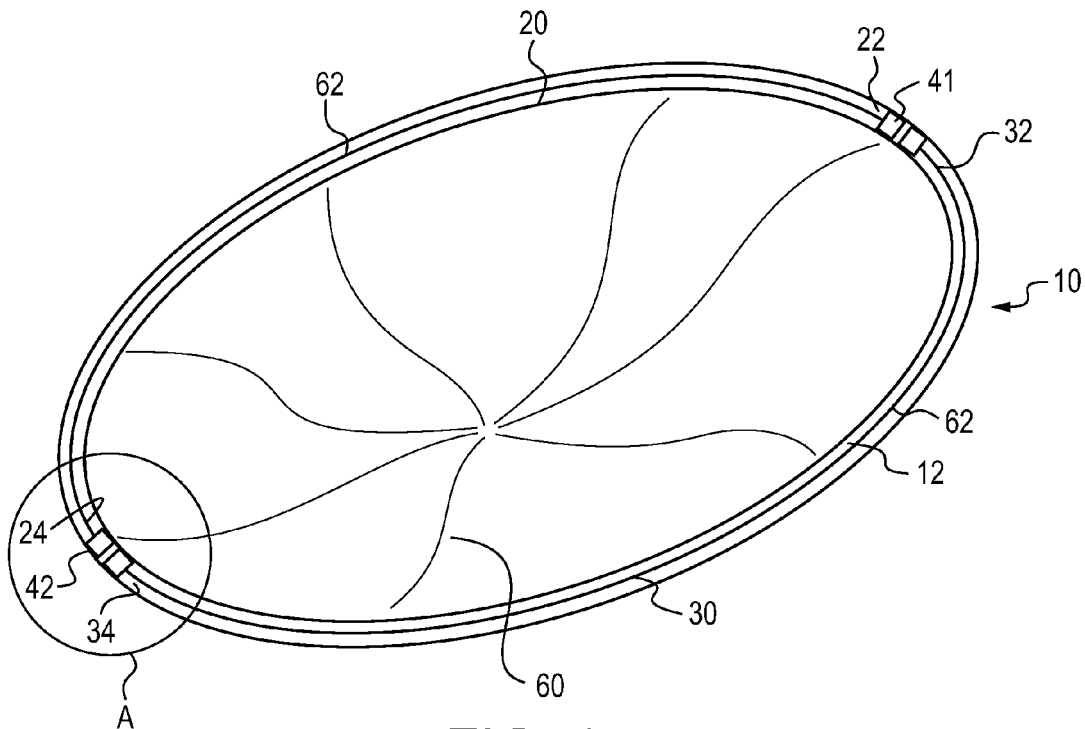
FIG. 1 is a perspective view of a foldable retractor in a first substantially planar configuration.

Turning now to FIGS. 1-11, a foldable and deformable retractor 10 is provided. The retractor includes a frame 12 that is defined from hingedly connected first and second arms 20, 30, and includes a membrane 60 that is fixed to the first and second 20, 30 arms and encloses an opening defined between the first and second arms 20, 30 when the frame 12 is in the open configuration, i.e. the first configuration.

To deploy the retractor 10 within the patient, the first and second arms 20, 30 of the frame 12 is pivoted to a second configuration (FIG. 4) and may be positioned in a third configuration (FIG. 5) when the retractor 10 is to be passed through a small lumen, such as the lumen of a laparoscopic port 200, and then transferred into the patient and deployed to form a barrier of viscera or other neighboring tissue away from the desired surgical field.

The forces between the retractor 10 and the wall of the body cavity, or viscera or other tissue contacting the retractor 10 (shown schematically as forces F and G in FIGS. 7 and 8) make the retractor 10 self-retaining inside the cavity while correspondingly forming a working space adjacent the retractor 10. The frame 12 supports the membrane 60 attached thereto such that the membrane 60 forms a barrier against relevant organs inside the cavity to create a working space inside the cavity. The surgical procedure can then be performed inside the working space with the retained organs out of the way. The frame 12 and membrane 60 can be shifted around inside the body cavity to create different working spaces to facilitate differing steps in the surgical procedure. The membrane 60 additionally may be transparent to allow a surgeon or medical professional to inspect the retracted organs during surgery. After the surgery, the frame 12 and membrane 60 are deformed (to either the second configuration or the third configuration) and then removed from the body cavity through the surgical opening.

The retractor 10 can be used in a variety of surgical procedures including, for example, surgery of the GI tract, urinary system, reproductive system, abdominal wall, or pelvic floor. The retractor 10 can be used for laparoscopic surgery as well as open surgery and is particularly suited for open laparotomy, mini-laparotomy, pure laparoscopic surgery, hand assisted laparoscopic surgery (HALS), or single incision laparoscopic surgery (SILS). The retractor 10 can be used in human subjects or can be adapted for veterinarian use.

One exemplary surgical procedure involves abdominal surgery. During abdominal surgery, small bowel loops can fall into the pelvis and lower abdomen if unrestrained, obscuring the surgical field. This is especially true during less invasive surgery such as HALS, SILS and other Laparoscopic procedures. The retractor 10 may be deployed inside the abdominal cavity and retract the small bowel out of the lower abdomen and pelvis, thus facilitating the surgery.

The retractor 10 may be configured to assist with other surgical procedures including laparoscopic or open sigmoid colectomy, ileocolic resection, hysterectomy, pelvic floor repair or resection fixation, or repair of the rectum or bladder. The retractor 10 may be inserted into the abdominal cavity of a patient undergoing surgery via a SILS, HALS or laparoscopic access device or even through an abdominal wall incision. Once deployed, the frame 12 assumes a generally ovoid shape within the peritoneal cavity, and is further urged into a convex form by pressure from the patient's lateral abdominal wall. During surgery, the frame 12 is held in place by means of anterior-posterior pressure exerted on the frame 12 by the anterior abdominal wall and posterior retroperitoneal structures. It is also held in place by lateral pressure exerted on it by the lateral abdominal wall and hence self-retaining. Having become "wedged" into the abdominal cavity, the membrane 60 (and/or the frame 12) exerts axial pressure on the abdominal viscera and prevents bowel loops from entering the surgical field.

The frame 12 is formed from first and second arms 20, 30 that are pivotably attached together with first and second hinges 41, 42. The first arm 20 includes a first end portion 22 and an opposite second end portion 24, and normally is oriented in an arcuate orientation therebetween, such as a half circle, half ellipse, a half bean, and the like. The second arm 30 includes a first end portion 32 and an opposite second end portion 34, and is normally oriented in an arcuate orientation therebetween, either in a similar orientation to the first arm 20, or in a differing or complementary orientation to facilitate both the desired frame structure when deployed within the patient, but to also provide a compact configuration when in one or both of the second and third configurations. Each of the first end portions 22, 32 of the respective first and second arms 20, 30 include first ends 22a, 32a that are disposed at the end tip of the respective first end portion 22, 32. Similarly, each of the second end portions 24, 34 of the respective first and second arms 20, 30 include second ends 24a, 34a that are disposed at the end tip of the respective second end portion 24, 34.

Figure 5:
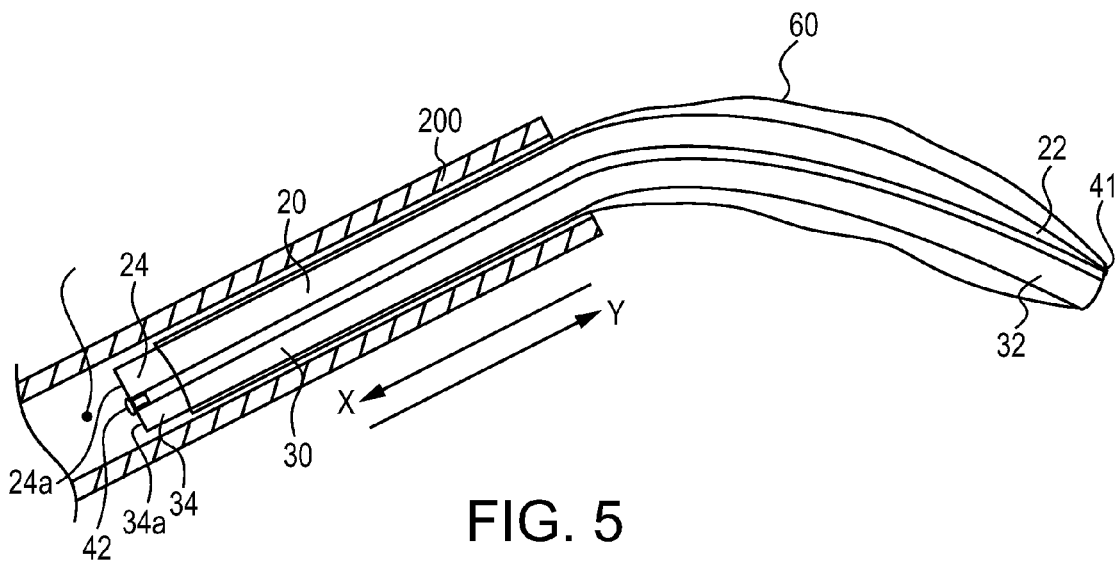
FIG. 5 is the retractor of FIG. 1, showing a proximal portion of the retractor being threaded through the lumen of a laparoscopic port, with the proximal portion of the retractor being in the third configuration.

The cross section of each of the first and second arms 20, 30 may be generally circular, or other shapes with appropriate strength-to-size ratios. The first and second arms 20, 30 may each have an outer diameter from about 0.1 cm to about 3 cm, inclusive of all dimensions within this range, in some embodiments from about 0.25 to about 2.5 cm, and in additional embodiments about 0.5 cm to about 2 cm in diameter. The cross-section of the first and second arms 20, 30 may be a function of the size of the port that (such as a laparoscopic port 200) that the retractor 10 is disposed therethrough to access the surgical field. The combined cross-section of the first and second arms 20, 30 and the compressed membrane 60 must be sufficiently small to fit through the desired port, yet the frame 12 and membrane 60 must retain the strength necessary to sufficiently retract the unwanted tissue within the surgical field, while retaining the flexibility to deform to the third configuration (FIG. 5). The first and second arms 20, 30 may be made from an elastomeric material, or a thin central member with an elastomeric coating, such as a formed by dip coating. The elastomeric material may cover the entire length of the one or both of the first and second arms, or may cover only a portion of one or both of the first and second arms 20, 30.

The frame 12 may establish a perimeter (when in the first configuration shown in FIG. 1) of about 0.25 cm to about 10 cm inclusive of all dimensions within this range, in some embodiments of about 0.5 cm to about 8 cm, and in additional embodiments of about 1 cm to about 6 cm. Generally, the frame 12 may be configured to be of appropriate diameter to be used in conjunction with various surgical fields within a human or mammal patient, with the specific size needed for the frame 12 determined by the anatomical size of the patient and their surgical field.

Figure 9:
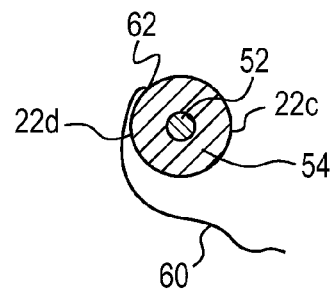
FIG. 9 is a cross-sectional view of the first arm taken of section C-C of FIG. 2.
Figure 10:
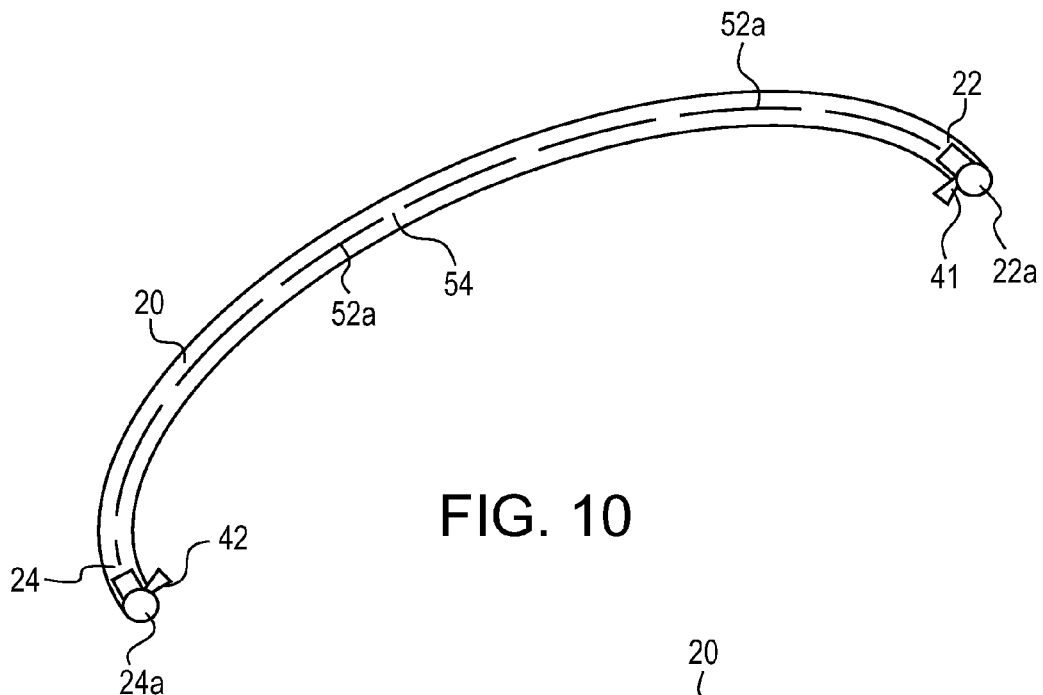
FIG. 10 is perspective view of a first arm of the retractor of FIG. 1, depicting a non-continuous superelastic element disposed upon the first arm.
Figure 11:
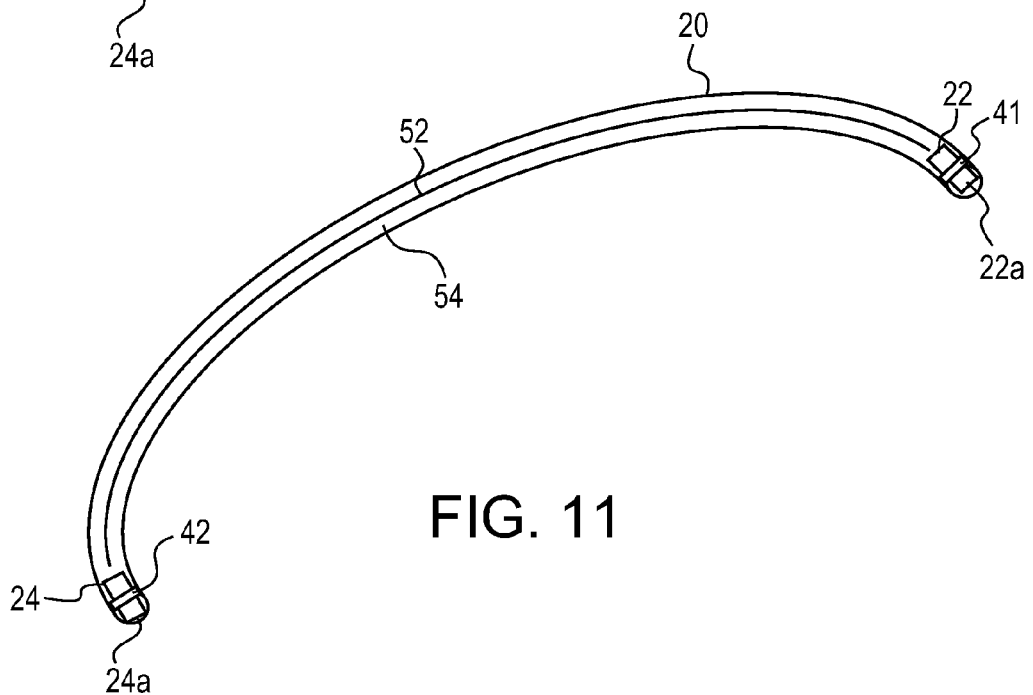
FIG. 11 is the view of FIG. 10, depicting a continuous superelastic element disposed upon the first arm.

With reference to FIGS. 9-11, the construction of the first and second arms 20, 30 may be formed in a similar manner and orientation to each other. FIG. 9 depicts a cross-sectional view of the first arm 20, which is representative of the cross-section of various positions along both the first and second arms 20, 30. Because the construction of the first and second arms 20, 30 are similar, for the sake of brevity the first arm 20 will be discussed in detail and the construction of the second arm 30 will be understood to be similar. The first arm 20 may include one or more elongate portions of a drawn wire 52 that provides strength as well as flexibility to the first arm 20. In the embodiment depicted in FIG. 9, the wire 52 may be provided through the center of the arm 20 along its length, while in other embodiments, the wire 52 may be provided at other positions within the cross-section of the arm 20, such as establishing or proximate to the inner surface 22c of the arm or establishing or proximate the outer surface 22d of the arm 20.

The arm 20 may further include a relatively soft elastomer 54 (specifically a material that is classified as an elastomer, or another similar material that may be molded, extruded or drawn with similar properties to an elastomer), that is molded or extruded in parallel with the wire 52. The elastomer 54 may partially or fully surround the wire 52. The elastomer 54 is provided to increase the cross-section of the frame 12 to prevent the arm 20 from cutting into a patient's tissue when in use, while maintaining the ability for the arm 20 to deform from the first configuration to the third configuration as desired and return to the first configuration when an external force is released (due to the presence of the wire 52, the membrane 60, the hinges 41, 42 or other forces (such as the force of the tissue upon the frame 12 or membrane 60) that urge the frame 12 into the first configuration). As discussed below, the elastomer 54 may be configured to retain portions of the edge 62 of the membrane 60 therein, with the edge 62 of the membrane 60 fixed to the elastomer 54 when the elastomer is initially formed about the wire 52, or the edge 62 of the membrane 60 may be fixed to the elastomer 54 after the arm 20 is formed.

The wire 52 may be formed from a superelastic material, such as nitinol, or various alloys thereof, Nickel/Cobalt/Chrome, or various alloys thereof, or the like, and maybe disposed along the length of the first arm 20. The superelastic material, or material that exhibits stress induced martensite (SIM) at room or body temperature, is configured to allow the arm 20 to be significantly deformed, such as by pulling first and second end portions 22, 24 in tension, or by otherwise urging the arm 20 into a relatively elongate and straight orientation as shown in FIG. 5, yet urging the first arm 20 to return to its normal arcuate shape when the constraining force to elongate the first arm 20 is removed. In some embodiments, the wire 52 may be multiple wires 52 that are threaded, braided, or knitted together for added strength or other properties. Alternatively, the wire 52 may be multiple wires 52 (each forming a single wire or multiple attached wires) that are disposed within the cross-section of the arm 20, but are positioned within different positions (i.e. top, center, right, left sides). In other embodiments, the wire 52 (or other structure disposed upon the first and/or second arms in place of the wire 52) may be formed from a shape memory material, such as a shape memory metal or a shape memory polymer.

In other embodiments, the wire 52 may be substituted by a relatively elastic but high strength material, such as elongate stainless steel to provide the first arm 20 with the ability to significantly elastically deform between the first configuration (FIG. 1) and the third configuration (FIG. 5). In some embodiments shown in FIG. 10 the wire 52 may be formed from multiple wire segments 52a that are positioned within the first arm 20 (either at consistent spacing, or at differing spacing as needed) and are trained to urge the first arm 20 into the normal arcuate configuration. In embodiments with multiple spaced wire segments 52a, the differing wire segments may be formed from different materials, different wire thicknesses, differing number of wires 52a threaded, braided or knitted together, or the like to establish differing flexibility and resiliency characteristics along the length of the first and/or second arms 20, 30 for predetermined differing operation of the frame 12 when placed within the surgical field. Alternatively, as shown in FIG. 11, the wire 52 may be disposed along the entire length of the first arm 20.

Figure 1A:
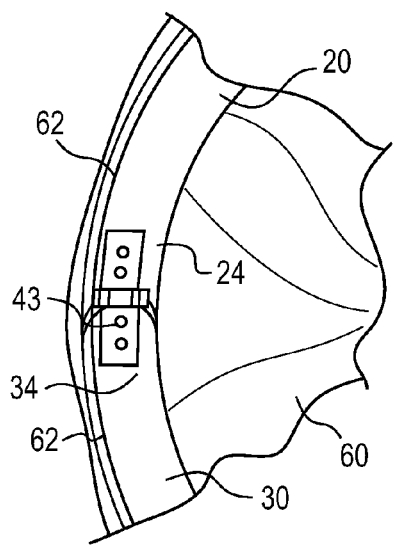
FIG. 1a is the view of detail A of FIG. 1.
Figure 1B:
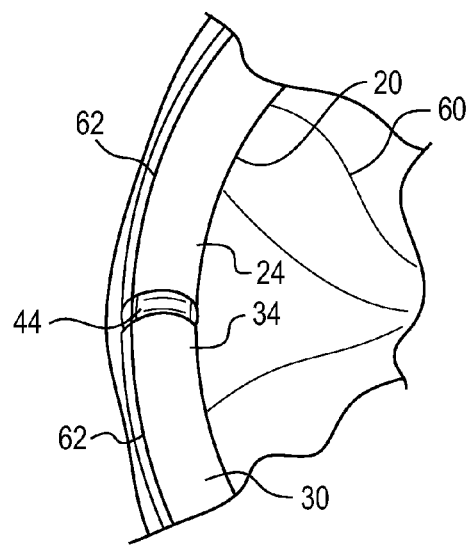
FIG. 1b is the view of FIG. 1a, depicting a living hinge connecting the second end portions of the first and second arms.

As best shown in FIGS. 1a and 1b, the first end portions 22, 32 and the second end portions 24, 34 are hingedly connected together, which allows the first and second arms 20, 30 to pivot with respect to each other from the first configuration (FIG. 1) where the first and second arms 20, 30 may be substantially disposed within the same plane (or in other orientations (such as residing in multiple planes) that are configured to be deployed within the surgical cavity), with the opposed first ends 22a, 32a and the opposed second ends 24a, 34a mating each other (or closely separated from each other) to form butt joints. Alternatively or additionally, the first and second end portions 22, 32 and 24, 34 may each be disposed with respect to each other such that the first and second arms 20, 30 in combination form a substantially continuous arcuate shape. In some embodiments shown in FIG. 1b, the second end portions 22, 32 of the first and second arms 20, 30 may be connected together with a living hinge 44. The first end portions 22, 32 may be connected together with a living hinge 44, in addition to or instead of the second end portions 24, 34.

Figure 1C:
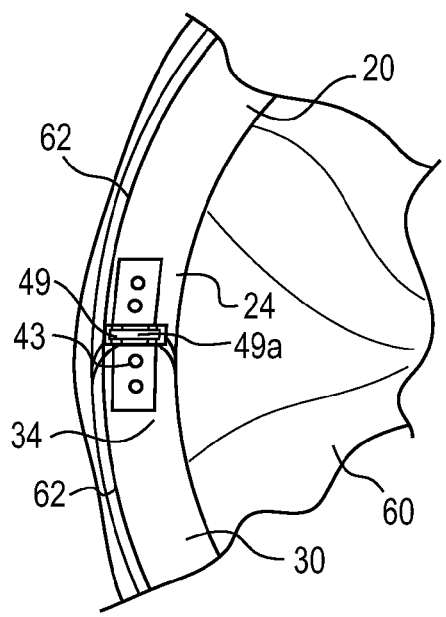
FIG. 1c is the view of FIG. 1a with a locking feature positioned to allow for retractor transition between folded and open configurations.
Figure 1D:
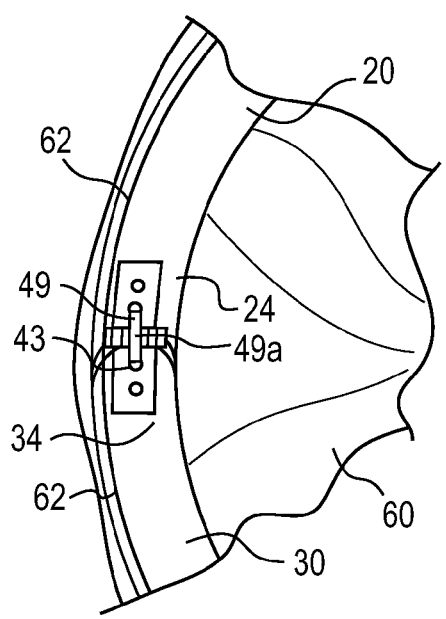
FIG. 1d is the view of FIG. 1c with the locking feature engaged to prevent the retractor from folding from the open position.
Figure 2:
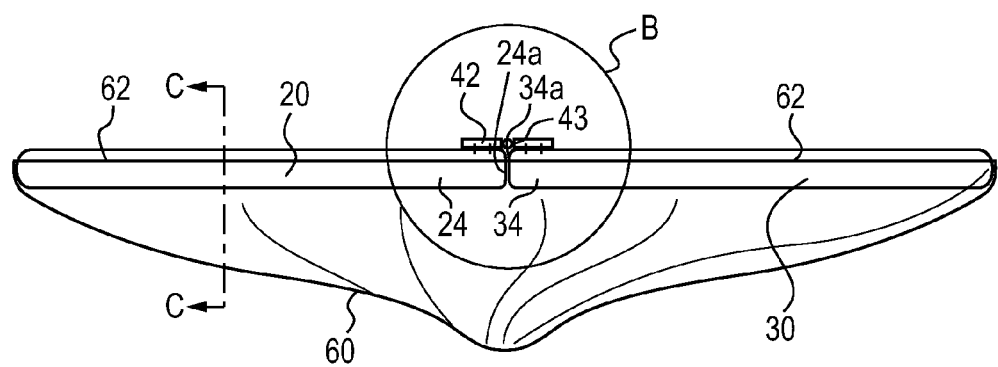
FIG. 2 is a side view of the retractor of FIG. 1.

Alternatively as best shown in FIG. 1a, the second end portions 24, 34 may be connected together with an external hinge 43, such as a piano hinge. The first end portions 22, 32 may be connected together with an external hinge 43 either in addition to or instead of the second end portions 24, 34. The hinged connections 41, 42 between each of the first and second ends 22, 32 and 24, 34 provides for controlled motion of the frame between the first configuration (FIG. 1) and the second configuration (FIG. 4) where the first and second arms 20, 30 are disposed side-by-side in substantially the same orientation, as discussed further below. In some embodiments shown in FIGS. 1c and 1d, the external hinge 43 may include a locking feature 49 that when engaged maintains the first and second arms 20, 30 in the first configuration even when the patient's tissue or other surgical environment may urge the arms away from this first configuration. The locking feature 49 may be a movable member fixed to the hinge (such as the central portion) that can be urged to interact with a receiving structure in another portion of the hinge. As depicted in FIGS. 1c and 1d, the locking feature 49 may be pivotably fixed to the central portion of the hinge 43 and aligned with the central portion when in a first position (to allow the hinge to fold and unfold) and may be rotated to a second position (normally substantially perpendicular to the first position) such that one or both opposite ends of the locking feature 49 rest upon the first and/or second ends 22, 32 and 24, 34 of the frame to prevent the hinge, and therefore the retractor from pivoting. The locking feature 49 may be urged between first and second positions by a tool (such as a forceps) that is typically used in a laparoscopic procedure.

Figure 6:
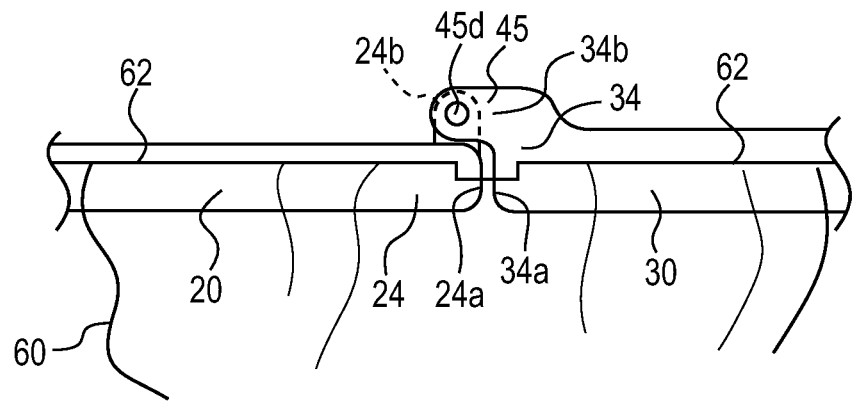
FIG. 6 is view of detail B of FIG. 2, depicting modified second ends of the first and second arms that are connected with a one-way hinge.
Figure 6A:
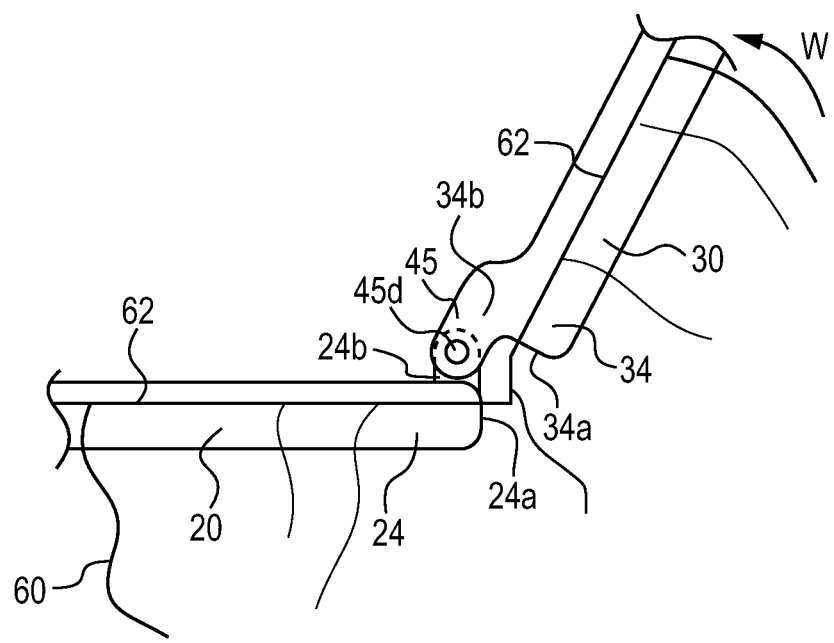
FIG. 6a is the view of FIG. 6, showing the first and second arms being folded toward the second configuration.

As shown in FIGS. 6a and 6b, one or both of the combined first or second end portions 22, 32 and/or 24, 34 may be configured to accept a one-way hinge 45, which allows one of the first or second arms 20, 30 to pivot with respect to the other arm (for example, in FIG. 6a the second arm 30 pivots with respect to the first arm 20 in the direction W), while the first and second arms 20, 30 are prevented from pivoting in the opposite direction with respect to each other. The one-way hinge 45 may be provided to assist the frame 12 from pivoting away from the first configuration when deployed within the patient, such that radial forces, and forces upon the frame 12 that are not purely in the radial direction, do not cause the first and second arms 20, 30 to pivot with respect to each other, therefore allowing the retractor 10 to continue to perform its function in the presence of external forces provided by the viscera or the patient's cavity.

The one way hinge 45 may be formed with a finger 34b that extends from the second end portion 34 of the second arm 30. The finger 34b extends past the second end 34a of the second arm 30 and extends above the second end 24a of the first arm 20. The tip of the finger 34b receives a pin 45d that is additionally received within a projection 24b that is formed from the second end portion 24 of the first arm 20. The second ends 24, 34 of the arms establish a butt joint. The position of the finger 34b and the projection 24b each prevent the first and second arms 20, 30 from pivoting with respect to each other in the opposite direction from that depicted in FIG. 6a.

One or both of the hinged connections 41, 42 between the two opposed ends of the first and second arms 20, 30 may be configured to urge the first and second arms 20, 30 into the first configuration when unconstrained. Specifically, the living hinge 44 may be configured with respect to the end portions that it connects to urge the first and second arms 20, 30 into the first configuration. Similarly, the external hinge 43 and/or the one-way hinge 45 may be configured with a spring or otherwise formed or connected to the opposed end portions to urge the first and second arms 20, 30 into the first configuration. The application of the biasing force by the hinged connections 41, 42 upon the first and second arms 20, 30 to urge the arms to the first configuration is shown schematically in FIG. 3 with the arrow Z depicting the direction of pivoting of the second arm 30 with respect to the first arm 20 to return the frame 12 to the first configuration when unconstrained. As discussed below, the membrane 60 may also be configured to urge the frame 12 into the first configuration when unconstrained.

In some embodiments, and as shown in FIG. 1, the frame 12 may be disposed in a first configuration where the first and second arms 20, 30 lie substantially within a single plane that passes through the center of each of the first and second arms 20, 30. Alternatively, the first and second arms 20, 30 may not be co-planar, but may be oriented in multiple planes or orientations to properly restrain tissue when deployed. Additionally or alternatively, the first and second arms 20, 30 may be substantially continuous throughout the length of each arm 20, 30 and substantially continuous along the transitions between opposite first and second end portions 22, 32 and 24, 34 of each of the first and second arms 20, 30 when in the first configuration. The frame 12 is normally positioned within the first configuration (or allowed to return to the first configuration) after the retractor 10 is positioned or deployed within the patient and proximate to the surgical field.

Figure 3:
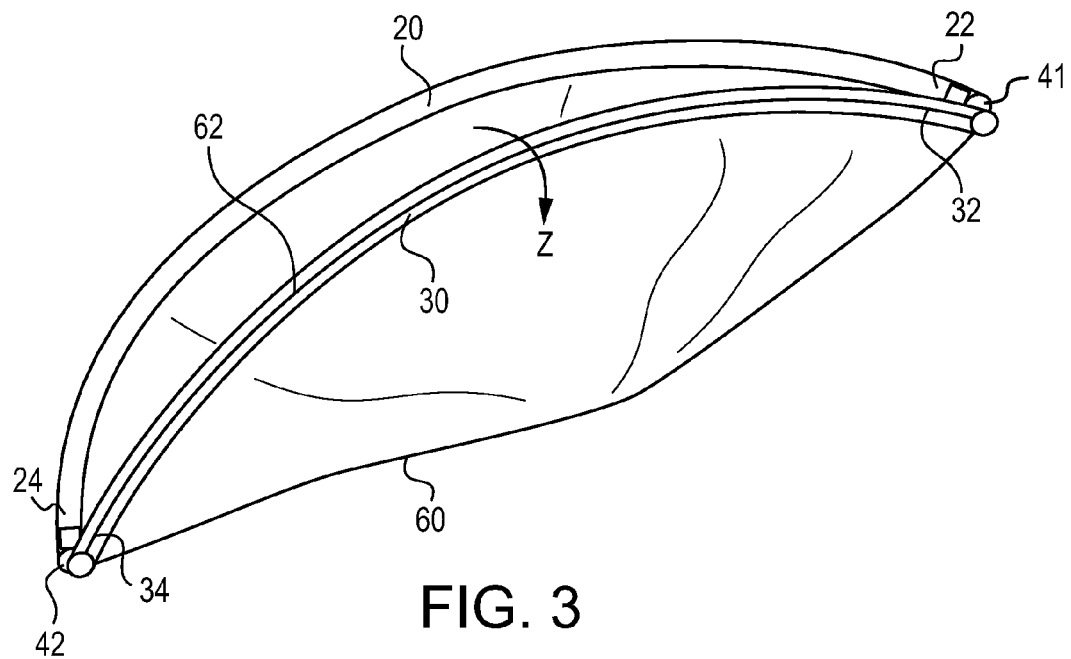
FIG. 3 is a perspective view of the retractor of FIG. 1, showing the retractor being folded in a position between the first and second configurations.
Figure 4:
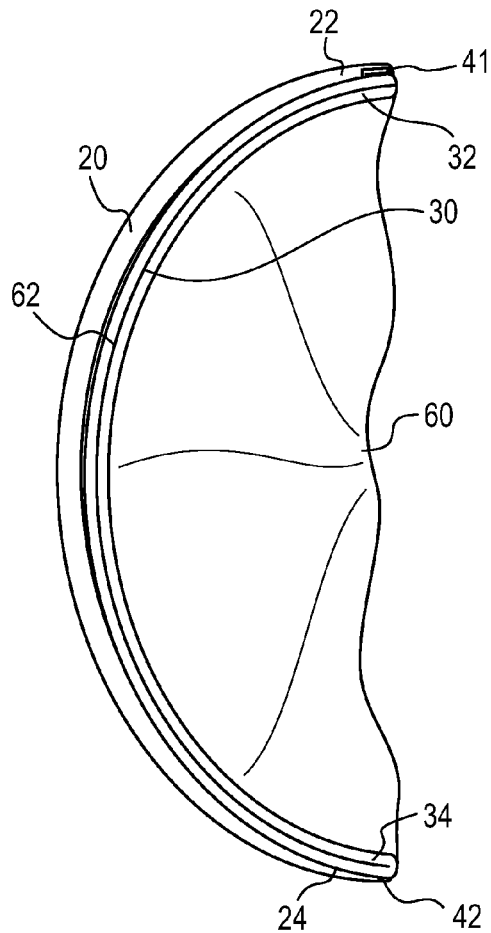
FIG. 4 is the retractor of FIG. 1, showing the retractor in the second configuration.

The first and second arms 20, 30 of the frame 12 may be pivoted with respect to each other as controlled by the hinged connections 41, 42 between the opposed first end portions 22, 32 and the opposed second end portions 24, 34. FIG. 3 depicts the first and second arms 20, 30 partially pivoted with respect to each other away from the first configuration, and FIG. 4 depicts the frame 12 in the second configuration with the first and second arms 20, 30 disposed in parallel to each other and closely spaced from each other (or contacting each other) along the length of the first and second arms 20, 30. The second configuration of the frame 12 is implemented to significantly decrease the cross-sectional area of the frame 12, to allow the frame 12 to be placed through a relatively small opening. In embodiments where the retractor 10 is inserted into the patient through an open incision (such as through a hand port), the retractor 10 may be passed into or out of the patient when in the second configuration.

As shown in FIG. 5, the retractor 10 is configured to be deformed from the second configuration and into a third configuration, wherein the frame 12 is disposed into an elongate and substantially straight orientation to allow the retractor to pass through a small lumen, such as through a lumen 201 of a conventional laparoscopic port 200. As the second end portions 24, 34 of the arms (and the hinge 42 connecting the second end portions 24, 34) are threaded into the lumen 201 in the direction X, the first and second arms 20, 30 are urged into the same straight orientation. As the frame 12 continues to be threaded through the port, the additional portions of the first and second arms 20, 30 that are threaded through the lumen 201 of the port is urged into the elongate configuration. When the frame 12 leaves the lumen 201 of the port 200 (either by being withdrawn from the port 200 in the direction Y, or by entering the surgical field through the inner end of the port 200), the frame 12 returns to the second configuration, due to the bias of the wire 52 disposed within the first and second arms 20, 30 as well as the restoring force of the hinges 41, 42.

The retractor 10 includes a membrane 60 that is connected or affixed to the first and second arms 20, 30 such that the membrane 60 is disposed within the opening defined between the first and second arms 20, 30. The membrane 60 may be made from of a biocompatible sheet, fabric, net or a combination thereof. The membrane 60 may be clear, transparent, translucent, opaque and made of a variety of different materials with different characteristics. In one embodiment, the membrane 60 can be made from an elastomer such as polyisoprene, polyurethane, silicone polyurethane, or silicone. In some embodiments, the membrane 60 may be non-elastic or only slightly elastic so that the membrane 60 can restrain organs or other body portions without significantly distending the membrane 60. Thus, inelastic materials such as polyethylene terephthalate can be used to form the membrane or portions thereof. The thickness of the membrane 60 may vary, for example, from about 0.005 inches (0.0127 cm) to about 0.1 inches (0.254 cm), inclusive of all thicknesses within this range, and in some embodiments of about 0.01 inches (0.0254 cm) to about 0.05 inches (0.127 cm). A person of ordinary skill in the art will recognize that additional ranges of thickness within the explicit ranges above are contemplated and are within the present disclosure.

In general, the membrane 60 is secured around majority or all of the frame 12 and at least a portion of the membrane 60 generally remains attached to the frame 12 as the first and second arms 20, 30 are manipulated between the first, second, and third configurations. In some embodiments, the membrane 60 may contain perforations for accessing the retracted organ during the surgery. Alternatively, the membrane 60 can be made of material that can be punctured through by surgical instruments. A range of materials can be used for the membrane 60 as described herein, and the membrane can be relatively impermeable or the membrane 60 can have pores or an open weave, as long as the membrane 60 functions to restrain selected organs in conjunction with the frame 12.

The membrane 60 may be secured directly to the opposed first and second arms 20, 30 with the edge 62 of the open end of the membrane 60 being bonded, affixed, or otherwise attached to the first and second arms 20, 30. In some embodiments, the edge 62 of the membrane 60 is affixed to the arm during the extrusion or molding process of the arm. Alternatively, the edge 62 of the membrane may be sealed to the first and second arms 20, 30 using an adhesive or heat sealing technique, or mechanically fixed to the arms 20, 30 using mechanical fasteners or stitches. Alternatively, the membrane may wrap around the first and second arms 20, 30 and sealed unto itself. The membrane 60 may be attached around a majority of the perimeter of the frame 12, although in some embodiments, the membrane 60 may be attached around the entire perimeter of the frame 12, either including or not including the hinged connections 41, 42.

The membrane 60 may be configured and attached to the first and second arms 20, 30 such that the membrane 60 urges the first and second arms 20, 30 of the frame 12 into the first configuration. The membrane 60 may be configured to urge movement of the first and second arms 20, 30 either by the size of the membrane 60, the flexibility of all, or only localized portions to the hinges 41, 42, of the membrane 60. The membrane 60 is also configured such that forces G upon the membrane 60 (as shown schematically in FIG. 7) are transferred to the first and second arms 20, 30 to urge the frame 12 into the first configuration.

Figure 7:
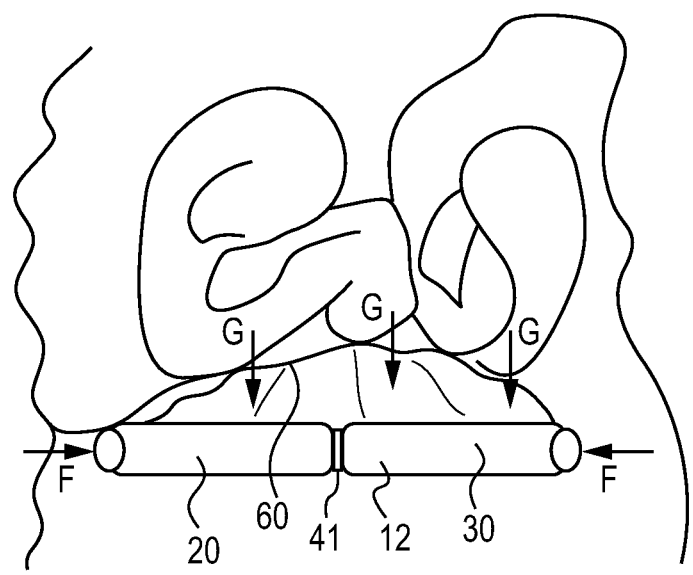
FIG. 7 is a schematic view of the retractor disposed entirely within the patient, and disposed such that the membrane urges the viscera into a withdrawn position from the surgical field.
Figure 8:
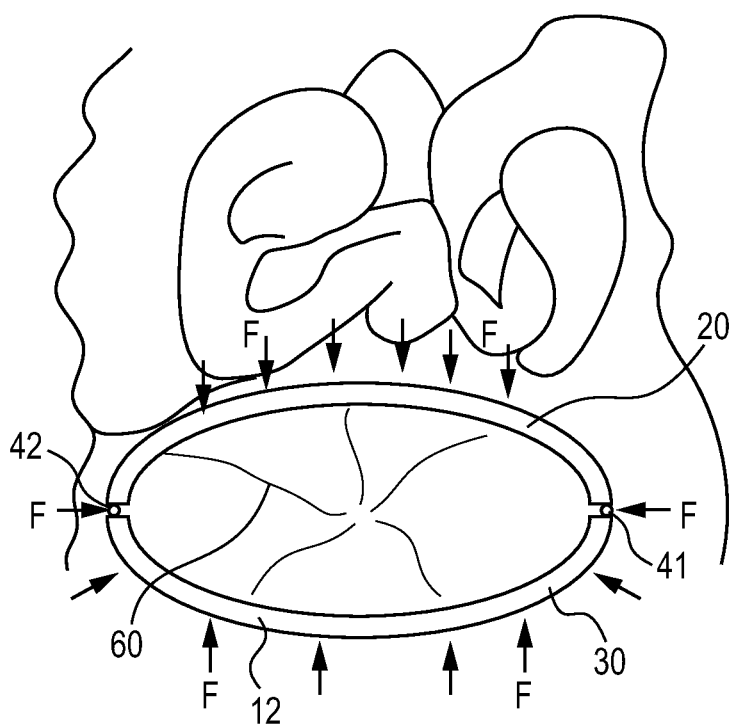
FIG. 8 is the view of FIG. 7, showing the retractor in an alternate configuration such that the combined first arm and membrane urges the viscera in a withdrawn position from the surgical field.

FIGS. 7 and 8 provide schematic views of the retractor 10 positioned within a patient and acting to separate viscera (such as bowel loops within the pelvic cavity) from the surgical field. In FIG. 7, the frame 12 is deployed in the first configuration such that the membrane 60 is pressed against the bowel loops and other viscera. Alternatively, FIG. 8 depicts the frame 12 deployed perpendicularly to the position depicted in FIG. 7, with the frame 12 itself pressing against the viscera. As shown in both FIGS. 7 and 8, the anatomical cavity and viscera (and other organs) provides inwardly directed radial force (schematically depicted with the arrows and element F) upon the frame 12. Similarly, as shown in FIG. 7, the viscera itself also provides a force upon the membrane 60 in situations where the membrane 60 provides a significant portion of the reaction force upon the retractor 10. As best understood with reference to FIGS. 7 and 8, the first and second arms 20, 30 (and the hinged connections 41, 42 therebetween) are constructed such that the frame 12 is maintained in the first configuration when feeling the largest anticipated reaction forces F or G upon the frame 12 and membrane 60. The frame 12 may be constructed to flex or somewhat deform in the presence of anticipated forces F or G, but the frame 12 maintains its general orientation to maintain the viscera separate from the surgical field as desired during a medical procedure.

Figure 12:
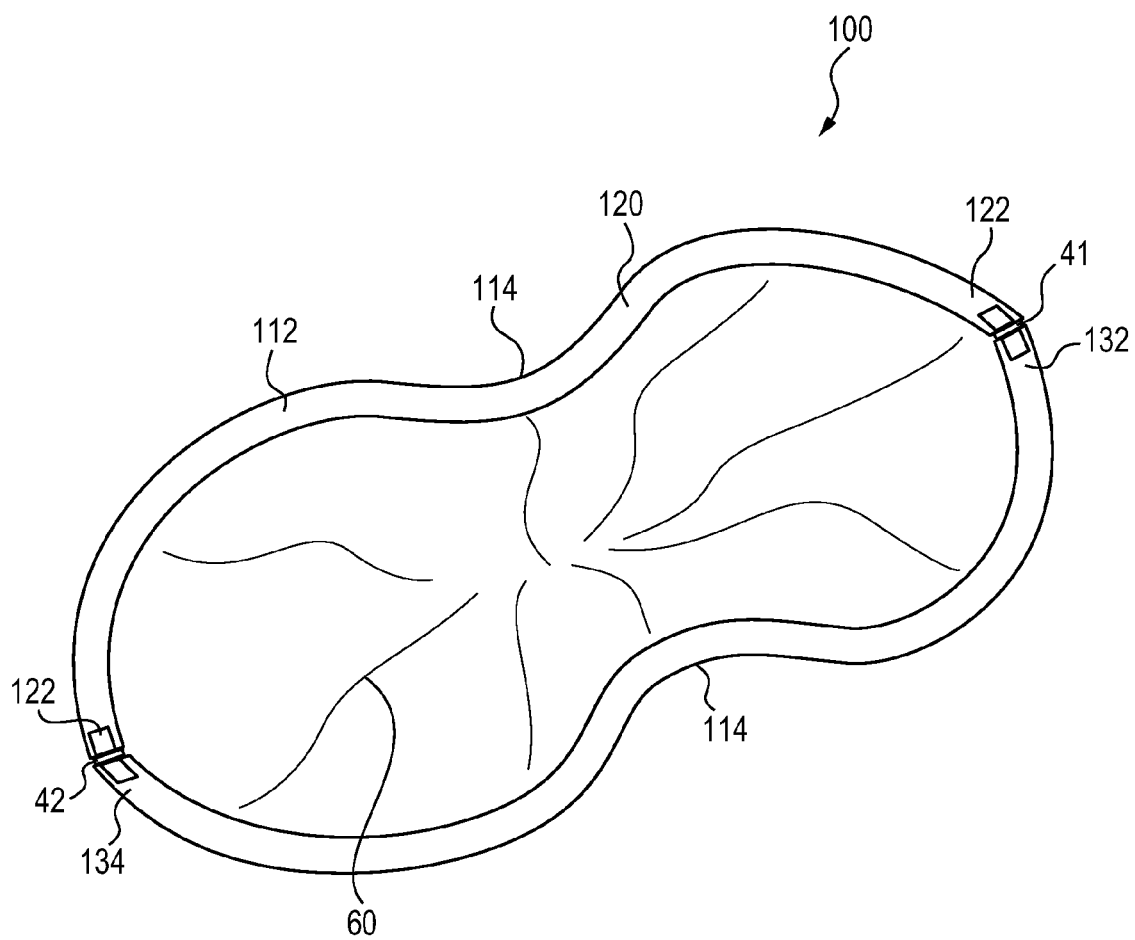
FIG. 12 is an alternate foldable retractor, depicting the first and second arms of the retractor shaped with both convex and concave portions.

In some embodiments, the frame 12 may be constructed to establish a shape other than the generally circular or elliptical shape of FIG. 1. For example, as depicted in FIG. 12, the retractor 100 may include a frame 112 that is formed as a "bean" shape, with a majority of the perimeter formed with a "convex out" profile, but with one or more "concave out" sections 114 disposed upon the frame 112. The concave out portions of a "bean shaped" frame, when deployed inside a body cavity, may be oriented, for example, such that the concave out section 114 is proximate a retroperitoneal vessel and/or conduit to prevent compression or occlusion of the vessel and/or conduit, while establishing compression upon the other anatomical structure in contact with the frame 112. As shown in FIG. 12, the retractor 100 is formed from first and second arms 120, 130 (which may be formed similarly to arms 20, 30), each with first and second ends 122, 132 and 124, 134 that are each hingedly attached with a hinge 41, 42 (or hinge-like structure discussed above with respect to the retractor 10). The frame 112 of the retractor 100 may support a membrane 60 that is like the membrane 60 discussed above. In still other embodiments, the frame of the retractor may establish other geometrical structures, such as a U-shape, FIG. 8, horseshoe, omega, square, rectangle, among other shapes that may be beneficial or specifically configured for placement and anatomical retraction within certain portions of a patient's anatomy.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

The invention claimed is:

1. A foldable retractor, comprising:
   an arcuate deformable frame defined from a first arm extending through a first portion of an outer circumference of the frame, and a second arm defining a remaining portion of the outer circumference;
   the first and second arms each including opposite first and second end portions, wherein the respective first end portions and the respective second end portions are hingedly connected together; and
   wherein the first and second arms of the frame are biased toward a first configuration wherein the combined first and second arms are aligned substantially continuously through the combined first and second end portions and the frame extends through substantially a single plane, further comprising a deformable membrane secured around at least a portion of the arcuate frame to form a continuous restraining structure across a central opening of the frame,
   wherein the first and second arms may be manipulated to a second configuration wherein the first and second arms substantially overlap each other, wherein when the frame is in the second configuration, the first and second end portions of each of the first and second arms may be pulled away from each other to transfer the frame to a third configuration wherein the first and second arms are substantially elongate and the retractor is capable of extending within a substantially straight lumen, and wherein the first and second arms are biased to return to the second configuration as the retractor is withdrawn from the lumen.

2. The foldable retractor of claim 1, wherein the membrane is configured to urge the first and second arms of the frame into the first configuration.

3. The foldable retractor of claim 1, wherein the first and second arms each comprise a superelastic material that extends substantially along a length of each portion.

4. The foldable retractor of claim 3, wherein the first and second arms each comprise an elastomeric material formed substantially along an entire length of the first and second arms, wherein the elastomeric material is mated with the superelastic material.

5. The foldable retractor of claim 1, wherein one or both of the first and second end portions are foldably attached together with a hinge, wherein each hinge is disposed upon the respective first end portions or second end portions of each arm, wherein one or both of the hinges are fixed to a locally convex edge of one or both of the first and second arms when the frame is in the first configuration.

6. A foldable retractor, comprising:
   an arcuate deformable frame defined from a first arm extending through a first portion of an outer circumference of the frame, and a second arm defining a remaining portion of the outer circumference;
   the first and second arms each including opposite first and second end portions, wherein the respective first end portions and the respective second end portions are hingedly connected together; and
   wherein the first and second arms of the frame are biased toward a first configuration wherein the combined first and second arms are aligned substantially continuously through the combined first and second end portions and the frame extends through substantially a single plane, wherein each of the respective first and second end portions are foldably attached together with a hinge, wherein each hinge is disposed upon the respective first end portions or second end portions of each arm, wherein each hinge is fixed to a locally concave edge of each of the first and second arms when the frame is in the first configuration.

7. The foldable retractor of claim 6, wherein the first and second arms of the frame are configured such that when in the frame is oriented in the first configuration and one or more radially inward forces act upon the frame, the orientation of the frame deforms radially inward but the first and second arms remain substantially within the same plane.

8. A foldable retractor, comprising:
   a relatively flexible arcuate frame comprising a first arm defining a first portion of a circumference of the frame, and a second arm defining a remaining portion of the circumference of the frame, each of the first and second arms comprising first and second end portions disposed upon opposite ends of the respective first and second arm, wherein each of the first end portions are hingedly connected together and each of the second end portions are hingedly connected together such that the frame is biased to a first relatively planar configuration, and the first and second arms may be folded with respect to each other to a second configuration wherein the first and second arms are disposed in substantially the same orientation;

further comprising a deformable membrane secured around at least a portion of the arcuate frame to form a continuous restraining structure across a central opening of the frame, wherein the membrane urges the first and second arms into the first orientation, wherein one or both of the hinged connections between each of the first end portions and each of the second end portions includes a lock that maintains the first and second arms in the first configuration.

9. The foldable retractor of claim 8, wherein the first and second arms of the frame each comprise an elongate superelastic material that urges the first and second arms into the first configuration.

10. The foldable retractor of claim 9, wherein the first and second arms of the frame each comprise an elastomeric material disposed upon a length thereof.

11. The foldable retractor of claim 8, wherein the frame and membrane are configured to be positionable entirely within a human or a mammal patient and proximate a surgical field within the patient.

12. The foldable retractor of claim 8, wherein when the frame is in the second configuration the first and second end portions of each of the first and second arms may be pulled in tension away from each other to place the frame in a third configuration substantially elongate for threading the retractor within a lumen.

13. The foldable retractor of claim 12, wherein the retractor is configured to be threaded through a laparoscopic port when in the third configuration.

14. The foldable retractor of claim 8, wherein when the frame is in the second configuration the retractor may be threaded through a lumen, which urges the frame to a third relatively elongate configuration.

15. A foldable retractor, comprising:
an arcuate deformable frame defined from a first arm extending through a first portion of an outer circumference of the frame, and a second arm defining a remaining portion of the outer circumference;
the first and second arms each including opposite first and second end portions, wherein the respective first end portions and the respective second end portions are hingedly connected together; and
wherein the first and second arms of the frame are biased toward a first configuration wherein the combined first and second arms are aligned substantially continuously through the combined first and second end portions and the frame extends through substantially a single plane,
further comprising a deformable membrane secured around at least a portion of the arcuate frame to form a continuous restraining structure across a central opening of the frame, wherein each of the respective first and second end portions are foldably attached together with a hinge, wherein each hinge is disposed upon the respective first end portions or second end portions of each arm, wherein one of the first and second hinges is fixed to a locally concave edge of each of the first and second arms when the frame is in the first configuration.

16. The foldable retractor of claim 1, wherein the first and second arms of the frame are configured such that when in the frame is oriented in the first configuration and one or more radially inward forces act upon the frame, the orientation of the frame deforms radially inward but the first and second arms remain substantially within the same plane.

* * * * *

UNITED STATES PATENT AND TRADEMARK OFFICE
CERTIFICATE OF CORRECTION

PATENT NO. : 8,758,235 B2  
APPLICATION NO. : 13/546123  
DATED : June 24, 2014  
INVENTOR(S) : Jacqueline A. Jaworek Page 1 of 1

It is certified that error appears in the above-identified patent and that said Letters Patent is hereby corrected as shown below:

In the Claims

In column 10, claim 7, line 58, after "such that when" delete "in".

In column 12, claim 16, line 32, after "such that when" delete "in".

Signed and Sealed this
Sixteenth Day of September, 2014

Michelle K. Lee
*Deputy Director of the United States Patent and Trademark Office*